United States Patent [19]

Gaba

[11] Patent Number: 5,697,907
[45] Date of Patent: Dec. 16, 1997

[54] SAFETY CATHETER

[75] Inventor: Rodolfo Gaba, Simi Valley, Calif.

[73] Assignee: Graphic Controls Corporation, Buffalo, N.Y.

[21] Appl. No.: 587,716

[22] Filed: Jan. 19, 1996

Related U.S. Application Data

[63] Continuation-in-part of Ser. No. 472,553, Jun. 7, 1995, Pat. No. 5,584,809, which is a continuation-in-part of Ser. No. 376,399, Jan. 23, 1995, Pat. No. 5,533,974, which is a continuation-in-part of Ser. No. 94,842, Jul. 20, 1993, Pat. No. 5,417,659.

[51] Int. Cl.$^6$ .................................................. A61M 5/00
[52] U.S. Cl. ............................ 604/110; 604/158; 604/198
[58] Field of Search ................................ 604/110, 198, 604/263, 192, 195, 158, 164, 165, 167

[56] References Cited

U.S. PATENT DOCUMENTS

| | | | |
|---|---|---|---|
| Re. 34,416 | 10/1993 | Lemieux | 604/164 |
| 4,728,321 | 3/1988 | Chen | 604/110 |
| 4,747,831 | 5/1988 | Kulli | 604/110 |
| 4,798,587 | 1/1989 | Willoughby | 604/110 |
| 4,986,811 | 1/1991 | Thead et al. | 604/110 |
| 4,995,871 | 2/1991 | Sasaki et al. | 604/110 |
| 5,187,850 | 2/1993 | McCammon et al. | 29/235 |
| 5,195,983 | 3/1993 | Boese | 604/192 |
| 5,279,581 | 1/1994 | Firth et al. | 604/198 |
| 5,322,517 | 6/1994 | Sircom et al. | 604/198 |
| 5,328,482 | 7/1994 | Sircom et al. | 604/164 |
| 5,334,158 | 8/1994 | McLees | 604/110 |
| 5,411,486 | 5/1995 | Zadini et al. | 604/198 |
| 5,417,659 | 5/1995 | Gaba | 604/110 |
| 5,447,501 | 9/1995 | Karlsson et al. | 604/198 |
| 5,466,223 | 11/1995 | Bressler et al. | 604/263 X |
| 5,549,558 | 8/1996 | Martin | 604/110 |
| 5,562,629 | 10/1996 | Haughton et al. | 604/158 |

*Primary Examiner*—John D. Yasko
*Attorney, Agent, or Firm*—Lyon & Lyon LLP

[57] ABSTRACT

A safety catheter assembly holds a catheter onto an assembly housing, to prevent exposure of the point of a used needle. A needle extending from a needle assembly. A needle point lock has a housing, a locking arm with a hook extending outside of the housing and a rear tab. A wheel within the housing is pushed against a ramp surface and the rear tab of the locking arm, by a spring. Alternatively, a spring biased retainer may be used. The needle extends through the housing and a hole or slot in the locking arm, and into the catheter. The hub of the catheter is held against the housing by the hook on the locking arm, until the needle is withdrawn into the housing, releasing the locking arm and allowing the hook to separate from the catheter hub. After the point of the needle has been withdrawn into the housing, it cannot be pushed back out as the needle slot moves out of alignment with the needle point. The needle also cannot be withdrawn from the back of the housing as the tab on the locking arm moves to allow the wheel to engage the needle with a wedging action. The catheter cannot be accessed until the needle point is withdrawn and safely locked within the housing.

6 Claims, 7 Drawing Sheets

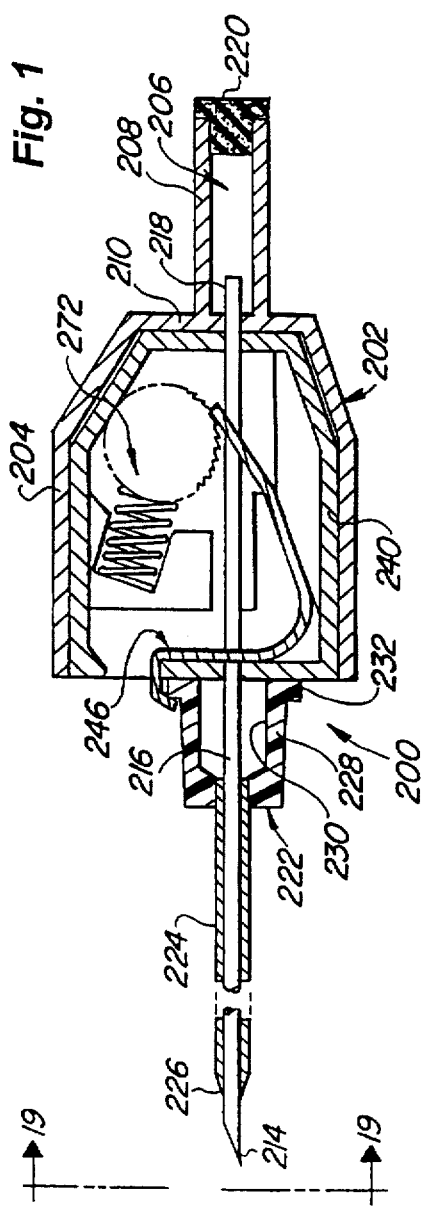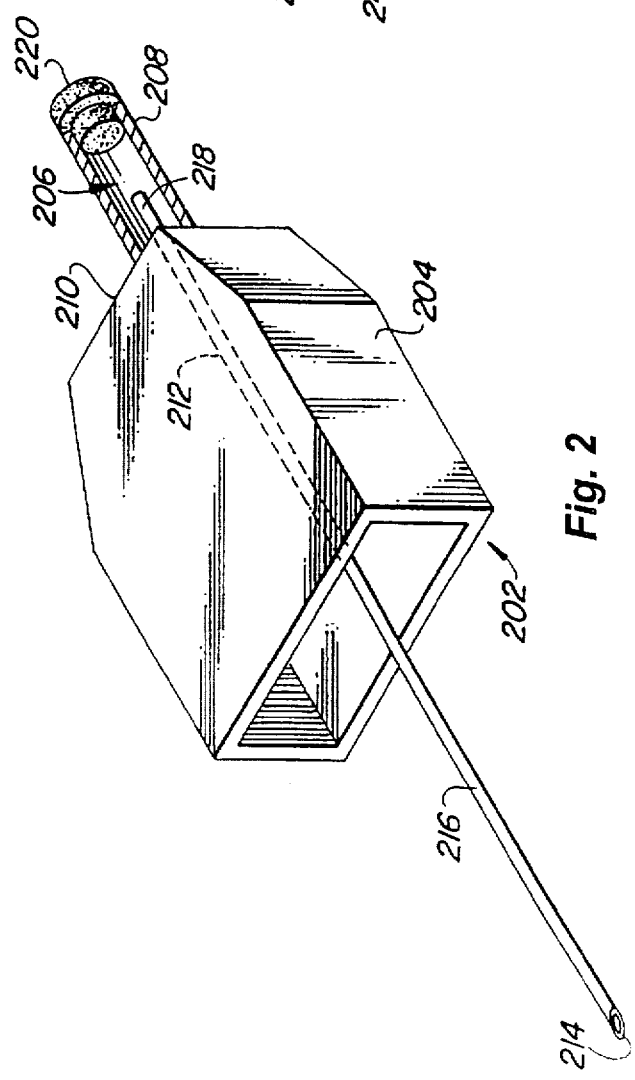

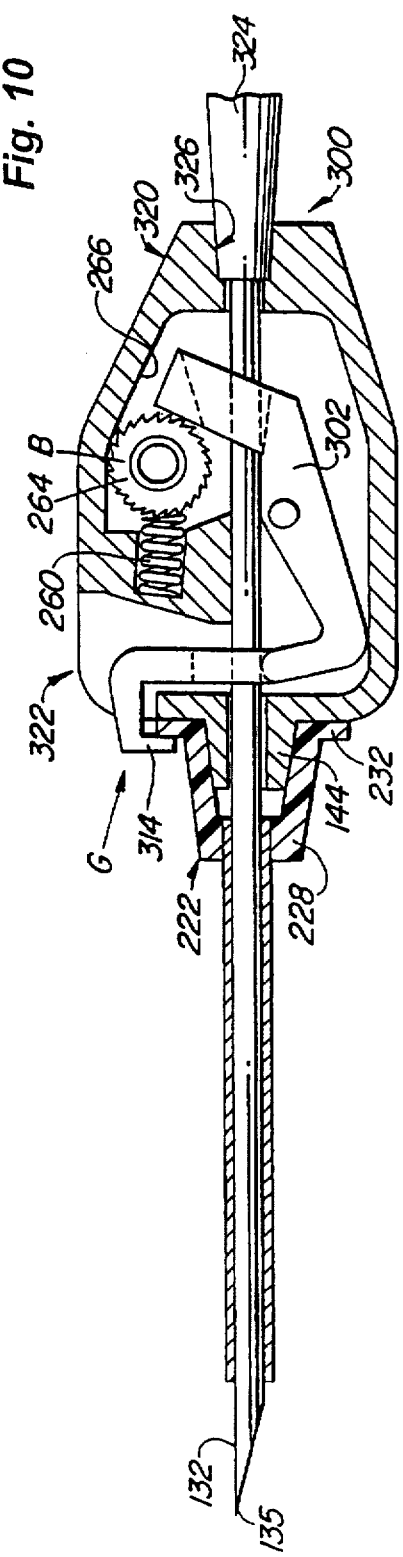
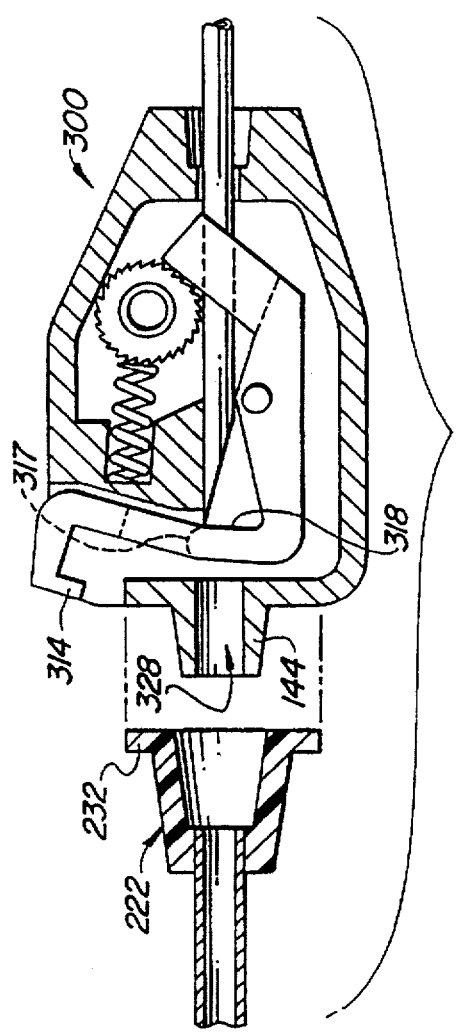
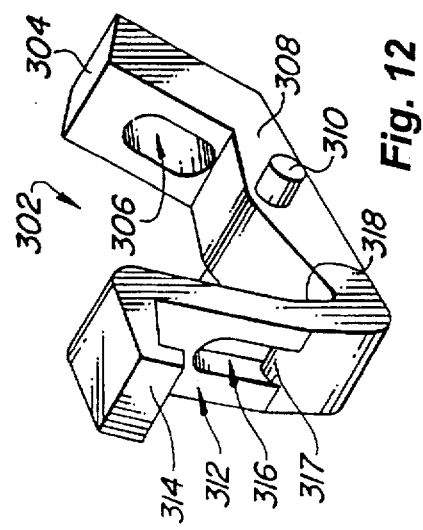

Fig. 13
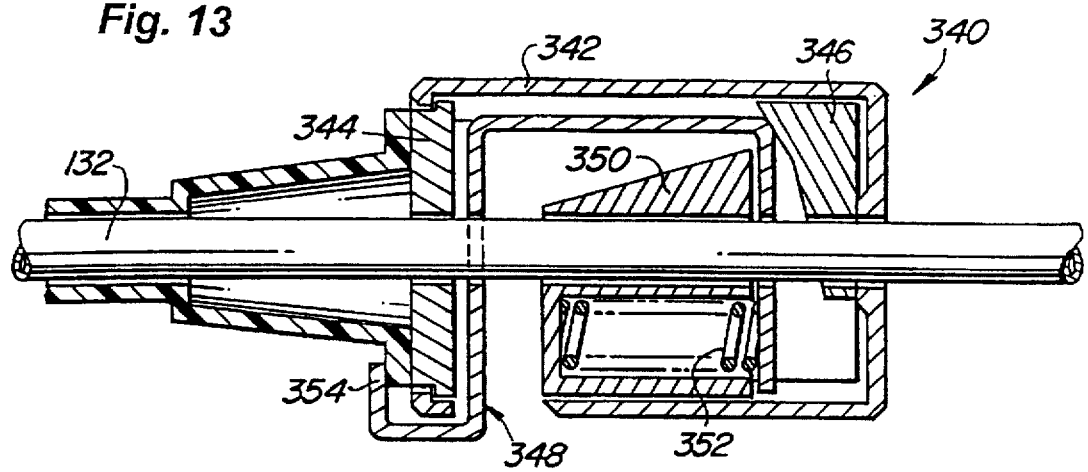
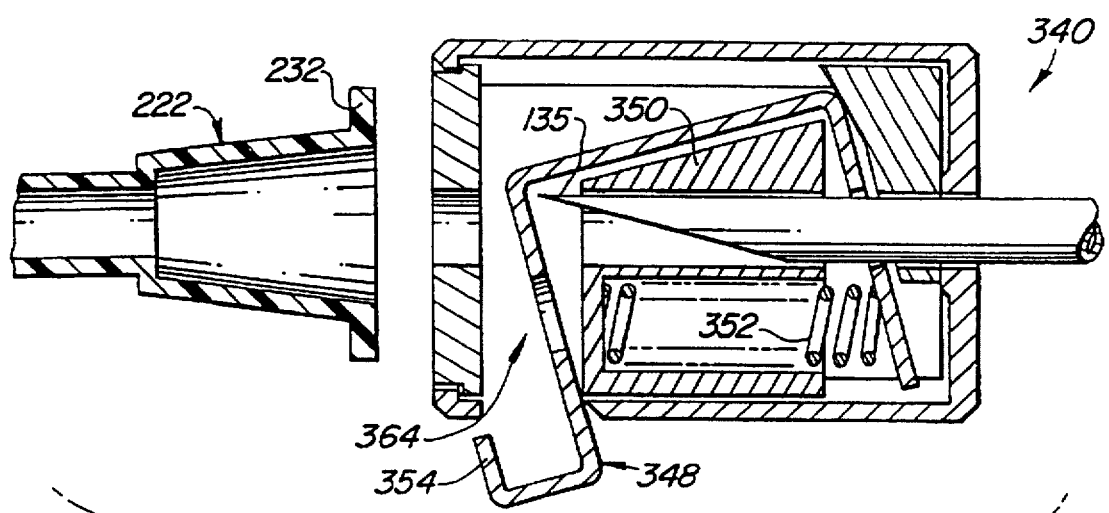
Fig. 14
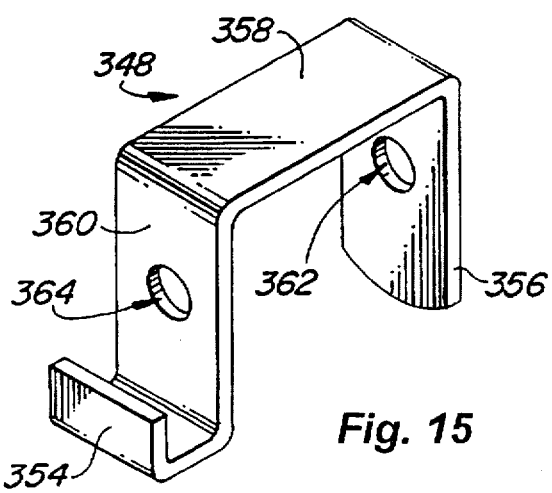
Fig. 15

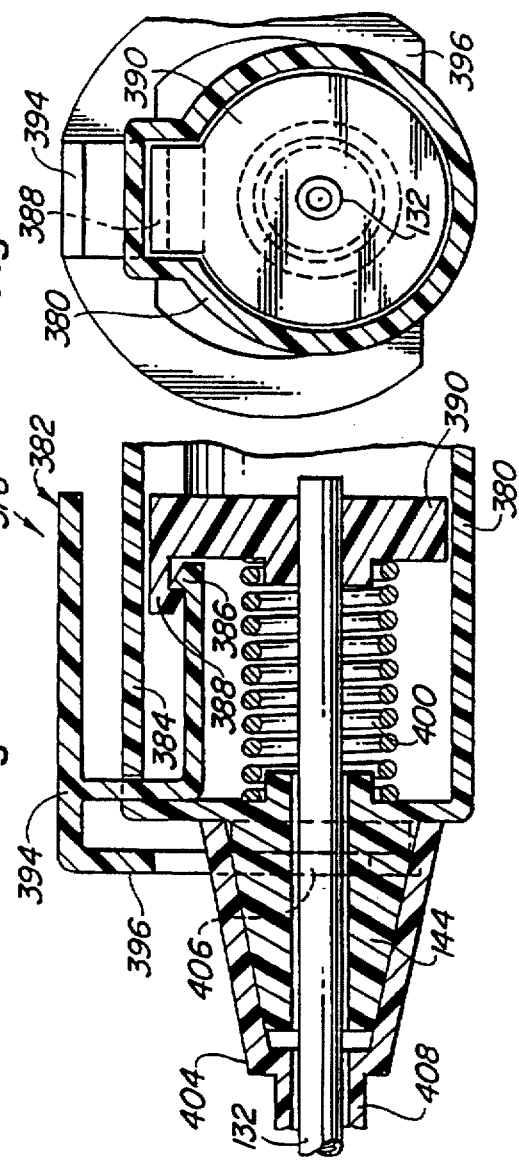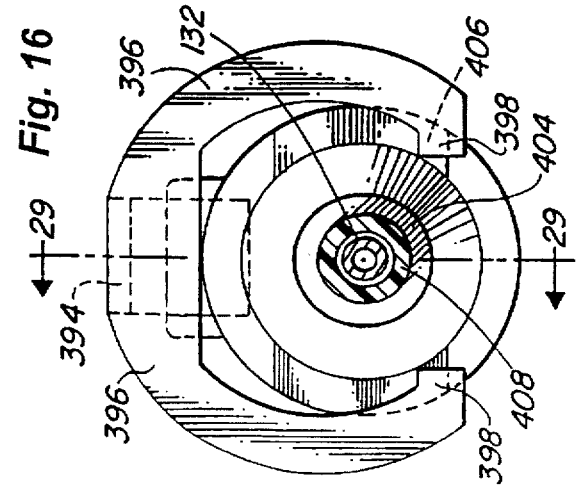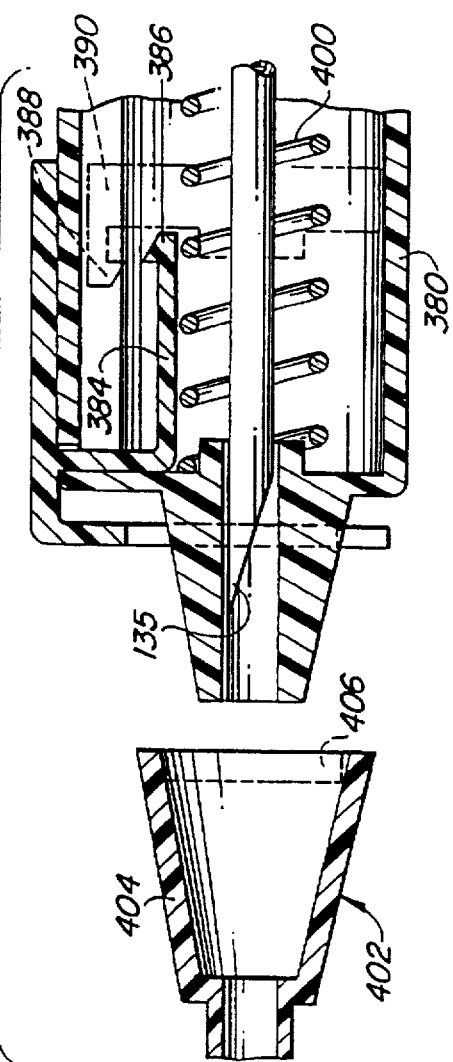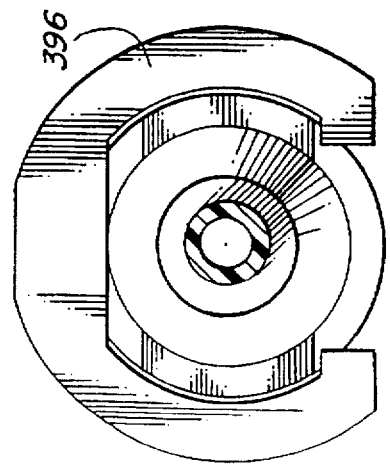

5,697,907

1

SAFETY CATHETER

This application is a continuation-in-part of Ser. No. 08/472,553 filed Jun. 7, 1995, now U.S. Pat. No. 5,584,809 which is a continuation-in-part of Ser. No. 08/376,399, filed Jan. 23, 1995, incorporated herein by reference, and now U.S. Pat. No. 5,533,974 which in turn is a continuation-in-part of Ser. No. 08/094,842, filed Jul. 20, 1993, and now U.S. Pat. No. 5,417,659, incorporated herein by reference.

BACKGROUND OF THE INVENTION

The invention relates to safety catheters. Catheters (i.e., a small tube or needle typically inserted into a vein) are widely used in hospitals to intravenously provide fluids such as blood, plasma, medication, etc. A catheter typically allows a number of intravenous (IV) tubes to be interchangeably connected, and is often left in a patient's arm even when not used, so that additional punctures need not be made for subsequent IV tubes or applications.

Catheters are generally inserted into the patient with a large-bore stylet or needle. In the most common configuration, the catheter is sold in a sterile pack with the catheter surrounding the needle. A removable plastic needle cover or cap may also be provided around the catheter and needle. In use, the plastic needle cover is first removed, the needle is used to puncture the patient's skin, and the needle and associated catheter are pushed into the puncture. The needle is then withdrawn from the patient and temporarily placed nearby while the catheter is held in place within the puncture site. Then, the catheter is taped to the patient and connected to the infusion set or other lines.

The need to immediately tape and connect an IV catheter generally takes priority over safe needle handling and disposal. The used needle may then be inadvertently left uncapped on a tray, bedsheet, cart, etc. Such a loose sharp instrument creates a significant safety risk to patients and medical personnel. Various types of so-called safety IV catheters have been previously provided to counter this problem. These devices usually include mechanisms designed to prevent needlesticks. However, conventional safety IV catheters tend to be bulky, difficult to use, and/or expensive. In addition, if not used correctly, their safety features can be inadvertently bypassed.

Accordingly, a need exists for an improved catheter which can be safely, quickly and reliably used and disposed of after use.

SUMMARY OF THE INVENTION

To these ends, in a first aspect of the invention, a safety IV catheter unit most desirably includes a point lock for covering the point of a sharp, i.e., a needle, trocar, scalpel, etc. The point lock preferably includes a housing, a wheel and a wedge surface. Once locked, the point lock prevents the sharp from being withdrawn from the housing. The instrument point or edge is therefore safely and virtually permanently contained within the housing. In a preferred embodiment, a locking arm is provided to prevent separation of the catheter from the point lock.

In an alternative preferred embodiment, a retainer having a push button preferably latches onto a slide attached to a needle. The push button advantageously has legs to hold the catheter against the housing. After the catheter is in position, the push button is pressed, advantageously releasing the slide from the latch and causing the needle point to be drawn into the housing, preferably via spring action.

In yet another aspect of the invention, the needle extends through a retainer in a housing. The retainer preferably has

2 a hook to secure the catheter to the front of the housing. The hook preferably remains engaged onto the catheter until the needle point is withdrawn into the housing. At that point, the hook releases the catheter and clamps onto the needle.

Other and further objects and advantages will appear hereinafter.

BRIEF DESCRIPTION OF THE DRAWINGS

In the drawings, wherein similar reference characters denote similar elements, throughout the several views.

FIG. 1 is a longitudinal section view of the present catheter unit or assembly;

FIG. 2 is a perspective view of the needle assembly of the catheter assembly of FIG. 1;

FIG. 3 is a section view of the needle point lock of the catheter assembly of FIG. 1;

FIG. 10 is a section view of an alternative embodiment safety catheter assembly, with the catheter and needle positioned for placement into a patient;

FIG. 11 is a section view of the embodiment of FIG. 10 with the catheter separated from the catheter assembly housing;

FIG. 12 is a perspective view of the retainer shown in FIGS. 10 and 11;

FIG. 13 is a section view of another embodiment, showing the catheter secured onto the catheter assembly housing;

FIG. 14 is a section view of the embodiment of FIG. 13 with the catheter separated from the housing;

FIG. 15 is a perspective view of the retainer shown in FIGS. 13 and 14;

FIG. 16 is a front elevation view of yet another preferred embodiment;

FIG. 17 is a section view taken along line 17—17 of FIG. 16, and showing the needle and catheter ready for placement into a patient, with the catheter secured onto the catheter assembly housing;

FIG. 18 is a cross-sectional end view thereof;

FIG. 19 is a front elevation view showing the push button of FIGS. 16–18 in the released position; and FIG. 20 is a section view thereof, with the alternative positions of certain components indicated in phantom line.

DETAILED DESCRIPTION OF THE DRAWINGS

Figure 4:
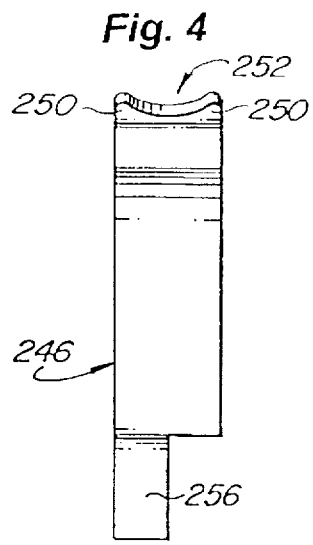
FIG. 4 is a front elevation view of the locking arm of the catheter assembly of FIG. 1.

Referring now in detail to the drawings, as shown in FIG. 1, the present safety catheter assembly or unit 200 includes a needle assembly 202, a needle point lock 240 and a catheter 222. As shown in FIG. 2, the needle assembly 202 has a housing cover 204 forming an open interior space, to receive the needle point lock 240. A preferably clear tube 208 extends from the back wall 210 of the housing cover 204, and is capped off with a vent 220 made of an air porous material. The tube 208 forms a cylindrical flash back chamber 206. The bore 215 at the back end 218 of a needle 212 opens into the flash back chamber 206. The needle passes through and is held in position by the back wall 210, extends forward through and projects substantially beyond the housing cover 204, to a point 214. The length of the shaft 216 of the needle 212 is selected to cooperate with the catheter 222 used and the particular medical application of the safety catheter unit 200.

Figure 7:
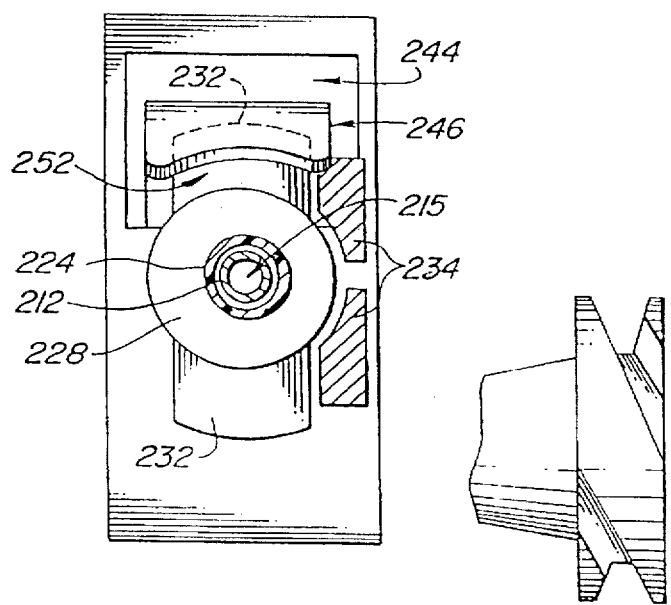
FIG. 7 is a front elevation view of the catheter assembly of FIG. 1.
Figure 7B:
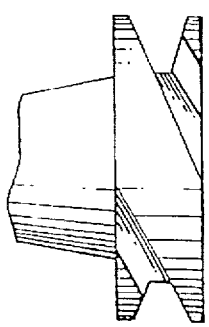
FIG. 7B is a partial side elevation view thereof.
Figure 7A:
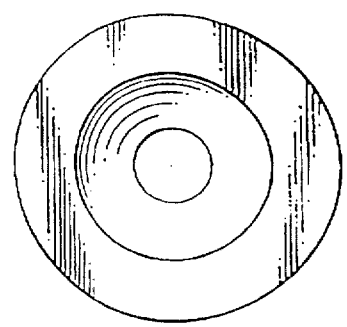
FIG. 7A is a rear end view of a full ring Luer lock on a standard catheter.

Referring once again to FIG. 1, the catheter 222 has a point 226, on a catheter shaft 224, having a hub 228 at the back end. The interior of the hub 228 has a fitting 230, such as a Luer fitting, adapted to connect with intravenous or other tubes or fittings. As shown in FIG. 7, the hub 228 of the catheter 222 includes Luer lock flanges 232, but may otherwise preferably be a full ring Luer lock 299 as seen in standard catheters.

Referring to FIG. 3, the needle point lock 240 has a housing enclosing a locking mechanism 272. The housing has a floor 280 and continuous walls, and a cover (not shown). A front opening 244 is provided in the flat front wall of the housing. A front needle hole 268 passes through the front wall of the housing 242, below the front opening 244, and is aligned with a rear needle hole 270 in the rear wall of the housing 242.

A spring block 284, a guide 286, and a shelf 282 are attached to or integral with the floor 280 and/or walls of the housing 242. The shelf 282 has a height which is only a fraction of the height of the housing 242, while the spring lock 284 and guide 286 preferably extend entirely from the floor 280 to the cover.

Figure 5:
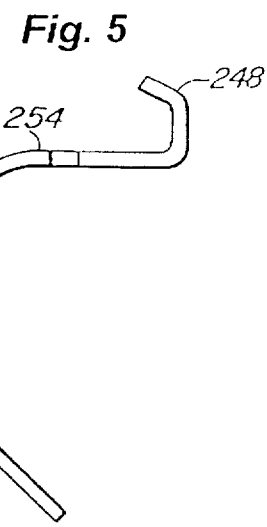
FIG. 5 is a side elevation view thereof.
Figure 6:
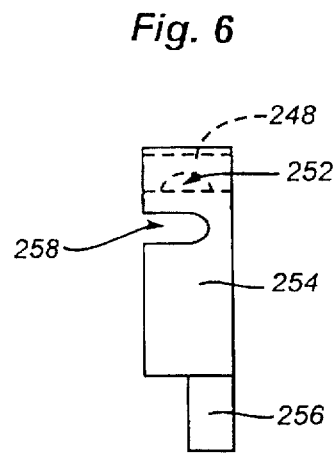
FIG. 6 is a rear elevation view thereof.

As shown in FIGS. 4, 5 and 6, a locking arm 246 has a hook 248 formed by prongs 250 on opposite sides of a cut out 252. The locking arm 246 is positioned within the housing 242 with a tab 256 on the locking arm 246 extending over the shelf 282. A needle slot or hole 258 is provided in the front leg 254 of the locking arm 246.

Referring to FIGS. 1 and 3, a spring 260 positioned within a spring bore 262 extends to push against a wheel 264, urging the wheel 264 against a ramp 266 on the housing 242, and against the tab 256 on the back end of the locking arm 246. The wheel 264 has a toothed, knurled, roughened or other engagement/friction surface.

Referring to FIG. 1, with the safety catheter 200 assembled and ready for use (e.g., as it would be provided in a sterile package), the housing cover 204 of the needle assembly 202 is positioned over and around the housing 242 of the needle point lock 240, with the needle 212 of the needle assembly 202 extending through the rear needle hole 270, through the needle slot 258 in the locking arm 246, through the front needle hole 268, and into and through the catheter 222. The diameter of the needle 212 is selected to fit closely within the catheter shaft 224, and the length of the needle 212 allows the point 214 to project just beyond the point 226 of the catheter shaft 224, as shown in FIG. 1. With the needle 212 extending through the needle slot 258, the hook 248 on the locking arm 246 is held down, clamping the rear flat surface of the hub 228 of the catheter 222 against the front flat surface of the housing 242. Referring momentarily to FIG. 7, flange stops 234 on the front surface of the housing 242 prevent rotation of the catheter 222, so that the flanges 232 on the hub 228 of the catheter cannot rotate or move out from under the hook 248 of the locking arm 246. If a full ring 299 Luer lock is used, flanges 232 are not needed as catheter rotation will not affect its retention by hook 248 of locking arm 246.

Figure 8:
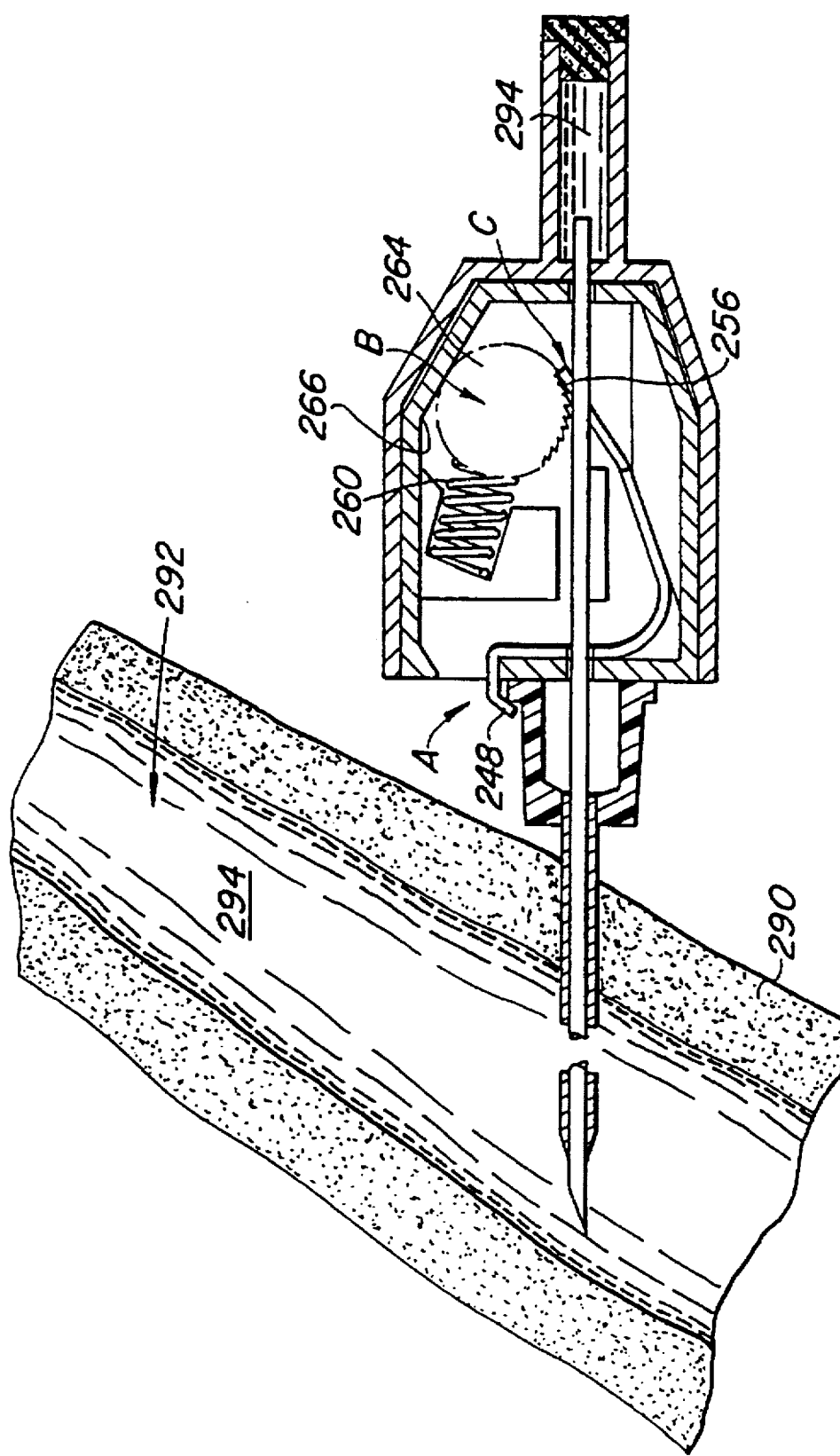
FIG. 8 is a side section view of the catheter assembly of FIG. 1 in use, inserted into a blood vessel.

In typical use, as shown in FIG. 8, the safety catheter 200 as it is shown in FIG. 1, is removed from its package. The needle 212, along with the catheter shaft 224 is pushed through the skin and tissue 290 into a blood vessel 292. Blood 294 flows through the hollow needle 212 into the flash back chamber 206. Air in the flash back chamber 206 is displaced by the blood 294 and diffuses out through the vent 220, which allows air, but not blood to pass through. The presence of blood 294 in the flash back chamber 206 provides a visual indication to the user.

Figure 9:
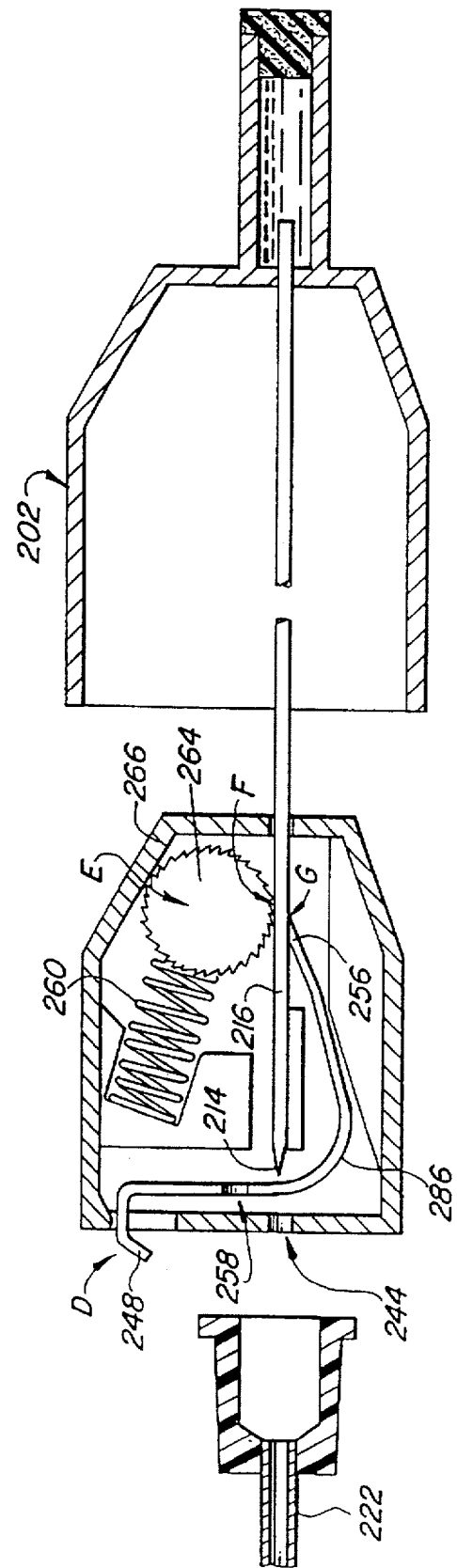
FIG. 9 is a side section view illustrating the locking features of the catheter assembly of FIG. 1.

Referring to FIGS. 8 and 9, while the catheter 222 is held in position, the needle assembly 202 is pulled back and separates from the needle point lock 240. The locking arm 246, in position A, keeps the needle point lock 240 attached to the catheter 222. The tab 256, in position C, holds the wheel 264, in position B, away from the needle. When the needle assembly 202 is pulled back sufficiently, the point 214 of the needle 212 is pulled within the housing 242, and out of or behind the needle slot 258. As soon as the point 214 clears the needle slot 258, the locking arm 246 springs up (position D in FIG. 9), driven by the spring tension of the locking arm 246 in the housing 242. The needle point lock 240 can then be removed from the catheter 222, so that an intravenous line can be connected to the catheter 222. As the needle slot 258 has shifted upwardly, as shown in FIG. 9, the needle 212 can longer be moved forward out of the housing 242. Trying to push the needle 212 forward, as shown in FIG. 9, simply drives the point 214 into a solid section of the front leg 254 of the locking arm 246. The needle 212 also cannot be pulled out of the rear of the housing 242, as the upward shift of the locking arm 246, from position A in FIG. 8 to position D in FIG. 9, also pivots or moves the tab 256 at the back end of the locking arm 246 downwardly (from position C in FIG. 8, to position G in FIG. 9), allowing the wheel 264 to engage against the shaft 216 of the needle 212, at position F in FIG. 9. Once released by the movement of the tab 256, the wheel 264, driven by the spring 260, now engages the needle shaft 216 and the ramp 266, rather than the tab 256 and the ramp 266. The roughened or toothed surface of the wheel 264 grips the shaft 216 of the needle 212, and the ramp 266, preventing the needle 214 from moving rearwardly out of the housing 242.

The needle shaft 216 cannot move away from the wheel 264 biased into the shaft 216, as the shaft 216 is supported at the rear needle hole 270, and by the guide 286. Rearward movement of the needle shaft 216 causes the wheel 264 to move down the ramp 266 and into further and stronger engagement against the shaft 216. The roughened or toothed surface on the wheel 264 prevents slipping between the needle shaft 216 and wheel 264. As a result, the point 214 of the needle 212 is safely contained within the housing 242. The needle point lock 240 and needle assembly 202 (connected by the needle shaft 216) can then be safely discarded.

Since the catheter 222 cannot be accessed until the needle assembly 202 is withdrawn, (thereby automatically safely locking the needle point 214 within the needle point lock housing 242) the point locking safety feature does not rely on the attention of the user.

Turning now to FIGS. 10–12, in an alternative embodiment the locking arm 246 shown in FIGS. 1 and 4–6 may be replaced by a retainer 302 pivotably mounted within a housing 320. Referring to FIG. 12, the retainer 302 has a back end 304 having a back slot 306. A retainer front end 312 is joined to the back end 304 by an arm 308. A front leg 318 on the front end 312 has a front slot 316 and a hook 314. A pivot pin 310 extends laterally from the arm 308, to pivotably mount the retainer 302 within the housing 320.

Referring to FIG. 10, a spring 260 urges a gripping wheel 264 onto a ramp surface 266, and into engagement with the back end 304 of the retainer 302. The hook 314 extends out of a top opening 322 in the housing 320. The hook 314 engages the hub 228 of the catheter 222, preferably engaging the Luer lock flanges 232, or alternatively the ring of a full ring Luer lock as is often used on standard catheters. The needle 132 extends through the housing 320, and through the back slot 306 and front slot 316 in the retainer 302. A tapered front fitting 144 on the housing 320 positions the hub of the catheter. A fitting 324 on the needle 132 may engage a tapered rear bore 326 in the housing 320, for added support.

As shown in FIG. 10, the safety catheter 300 is ready for use. With the retainer 302 in position G as shown, the catheter 222 cannot be separated from the housing 320. Accordingly, after the needle and catheter are placed into a patient, the needle must be withdrawn to access the catheter. Referring to FIG. 11, as the needle 132 is withdrawn, the floor 317 of the front slot 316 bears and slides against the underside of the needle, as it is urged into engagement of the needle via the spring 260 and wheel 264. However, this creates only a slight drag force which does not significantly effect withdrawal of the needle. Referring to FIG. 11, when the point 135 of the needle 132 moves behind the front slot 316, the retainer 302 pivots upwardly, releasing the hook 314 from the catheter 222. The catheter 222 and housing 320 can then be separated, so that connections may be made to the catheter. At the same time, the wheel 264 moves down the ramp 266 and engages the needle 132, and prevents further withdrawal of the needle from the housing 320. The needle cannot be pushed forward out of the housing 320 as the front housing opening 328 is now blocked by the front leg 318 of the retainer 302. Accordingly, the point 135 of the needle 132 is permanently secured within the housing 320, for safer handling and disposal.

Referring to FIGS. 13–15 an alternative embodiment improves the safety catheter described in U.S. Pat. No. 5,328,482, incorporated herein by reference. U.S. Pat. No. 5,328,482 describes a safety catheter using a lever arm of stiff material, formed in the general shape of a broad U of unequal proportions, as shown therein e.g., in FIG. 35. The embodiment 340 shown in FIGS. 13–15 allows the locking mechanism of U.S. Pat. No. 5,328,482 to be used with a catheter. Referring to FIG. 13, the safety catheter embodiment 340 has a sleeve or housing 342 with a front disk or guard body 344. A housing block 346 and a housing stand 350 extend upwardly and/or inwardly from the walls of the housing 344. A retainer 348 has a hook 354 extending out of the housing 344 to engage and hold the catheter to the housing. A spring 352 urges the retainer 348 to the rear of the housing 344.

Referring to FIG. 15, the retainer 348 includes a rear leg 356, arm 358, front leg 360 and the hook 354. A rear hole 362 in the rear leg 356 aligns with a front hole 364 and the front leg 360.

In use, the safety catheter 340 as shown in FIG. 13 is ready for placement into a patient. The hook 354 retains the catheter onto the housing 344. After placement, as shown in FIG. 14, the needle is withdrawn. When the point 135 of the needle is drawn behind the front hole 364, the retainer 348 pivots or shifts, freeing the hook 354 from the catheter, which can now be separated from the housing 344. The spring 352 shifts the retainer 348 into the position shown in FIG. 14. In this position, the point 135 of the needle cannot be pushed forward and out of the housing 344, as it is blocked by the front leg 360 of the retainer 348. The needle may not be withdrawn further from the housing 344, as the rear leg 356 frictionally locks against the needle, as described in U.S. Pat. No. 5,328,482.

Referring now to FIGS. 16–20, in yet another safety catheter embodiment 378, a slide 390 within a housing 380 has a catch 388. A retainer 382 has a push button surface 394. A tension arm 384 extending from the push button 394, through an opening in the housing 380, has a lip 386 engaged to the catch 388. A spring 400 has one end against a front wall of the housing 380 and pushes the slide 390 rearwardly. A pair of legs 396 with feet 398 extending downwardly or inwardly from the push button 394 overlap tabs 406 on a catheter 402, to secure the catheter to the front of the housing 380.

In use, with the safety catheter 378 in the position shown in FIG. 17, the needle and catheter are ready for placement. The tension created by the spring 400 on or through the slide 390 and retainer 382 maintain them in the positions shown. The catheter cannot be separated from the housing 380, as it is held in place by the legs 396 and feet 398 overlapping the tabs 406 on the catheter. After installation, to separate the catheter and housing, the push button 394 is pushed down or inwardly. This movement releases the catch 388 from the lip 386, as shown in FIG. 20. Simultaneously, the feet 398 move downwardly so that they are no longer over the catheter tabs 406. The catheter 402 is then free to move forward through the legs 396 and separate from the housing 380. The spring drives the slide 390 rearwardly to automatically withdraw the point 135 of the needle into the housing 380, where the needle may be safely contained for handling and disposal, e.g., as described in U.S. Pat. No. 4,747,831, incorporated herein by reference. The configuration of the legs 396 or feet 398 may be changed for use with a catheter having tabs or a pull ring.

Various of the features shown in the drawings may be used on the different embodiments described. For example, the needle assembly having the flash back chamber shown in FIG. 1 may also be used on the embodiments shown in the other figures. Different catheter hub configurations may also be used and alternative designs or materials may be substituted for the springs shown in the drawings. In addition, other equivalents of the retainers shown and described may also be used.

Thus, a novel safety catheter has been shown and described. Various modifications may of course be made without departing from the spirit and scope of the present invention.

I claim:

1. A safety catheter comprising:
    a housing having a front wall;
    a needle extending through the housing;
    a slide within the housing and attached to the needle;
    a catch on the slide;
    a spring positioned between the front wall of the housing and slide;
    a catheter around the needle;
    a retainer having at least one leg outside of the housing and holding the catheter against the front wall of the housing, and a tension arm extending into the housing and releasably attached to the catch on the slide.

2. The safety catheter of claim 1 further comprising a push button on the retainer.

3. The safety catheter of claim 1 further comprising a lip on the tension arm engaged to the catch on the slide.

4. The safety catheter of claim 1 wherein the retainer has a pair of legs, further comprising spaced apart tabs on the catheter and a foot on each leg, with the feet movable from a first position overlying tabs on the catheter, to a second position below and clear of the tabs, thereby releasing the catheter from the housing, with actuation of the retainer.

5. A safety catheter comprising:

a housing having a front wall;

a slide axially moveable within the housing;

a needle attached to the slide and extending out of the housing;

a spring in the housing pushing the slide away from the front wall;

a catheter on the front wall, outside of the housing and positioned around the needle; and a retainer having at least one leg outside of the housing and extending over the catheter, a tension arm inside of the housing engaging the slide, and a push button outside of the housing joined to the at least one leg and the tension arm.

6. A safety catheter comprising:

a housing having a front wall;

a slide in the housing moveable away from the front wall;

a needle attached to the slide and extending through the front wall;

a spring in the housing biasing the slide away from the front wall;

a catheter supported on the housing;

a retainer having a pair of spaced apart legs in front of the housing, a push button joined to the legs, and a tension arm joined to the push button and extending into the housing to engage the slide;

the retainer movable from a first position, where the push button is radially spaced apart from the housing and the legs of the retainer hold the catheter onto the housing and the tension arm holds the slide against movement away from the front wall, to a second position, where the push button is pressed radially inwardly towards the housing, thereby shifting the legs to release the catheter and shifting the tension arm to release the slide.

\* \* \* \* \*